United States Patent [19]
Lin et al.

[11] Patent Number: 4,824,988
[45] Date of Patent: Apr. 25, 1989

[54] PROCESS FOR RECOVERING CUPROUS IODIDE CATALYST USED IN SYNTHESIS OF (TRIFLUOROMETHYL)NAPTHALENES

[75] Inventors: Ronny W. Lin; Venkataraman Ramachandran, both of Baton Rouge, La.

[73] Assignee: Ethyl Corporation, Richmond, Va.

[21] Appl. No.: 112,398

[22] Filed: Oct. 26, 1987

[51] Int. Cl.$^4$ .................... C07C 121/62; C07C 69/76
[52] U.S. Cl. .................................. 558/423; 558/376; 558/425; 560/100
[58] Field of Search ...................... 558/376, 423, 425; 560/100; 423/42

[56] References Cited

U.S. PATENT DOCUMENTS 4,439,617  3/1984  Sestanj et al.
4,590,010  5/1986  Ramachandran et al. ......... 558/341

OTHER PUBLICATIONS

Matsui et al., "Chem. Letters", Chemical Society of Japan, (1981); pp. 1719-1720.

Primary Examiner—Joseph Paul Brust
Attorney, Agent, or Firm—Patricia J. Hogan

[57] ABSTRACT

In a process for preparing a (trifluoromethyl)napthalene by reacting a halonapthalene with a trifluoroacetate in the presence of cuprous iodide and a dipolar aprotic solvent and separating out the inorganic ingredients of the final reaction mixture in the recovery of the product, the cuprous iodide is recovered by washing the separated inorganic ingredients with an alcohol and a carboxylic acid and then with water to purify the cuprous iodide.

13 Claims, No Drawings

PROCESS FOR RECOVERING CUPROUS IODIDE CATALYST USED IN SYNTHESIS OF (TRIFLUOROMETHYL)NAPTHALENES

FIELD OF INVENTION

This invention relates to (trifluoromethyl)naphthalenes and more particularly to a process for recovering the cuprous iodide used in their synthesis.

BACKGROUND

As disclosed in U.S. Pat. No. 4,590,010 (Ramachandran et al.) and copending applications Ser. No. 808,304 (Lin et al.), filed Dec. 12, 1985, and Ser. Nos. 854,084 (Davidson I) and 854,085 (Davidson II), filed Apr. 21, 1986, it is known that (trifluoromethyl)naphthalenes can be prepared by reacting a corresponding halonaphthalene with a trifluoroacetate salt in the presence of cuprous iodide and a dipolar aprotic solvent. The products of these reactions can be recovered by conventional techniques, most satisfactorily by techniques which are conducive to isolation and recycle of the dipolar aprotic solvent and the cuprous iodide. However, it has been found that not all cuprous iodide recovery techniques lead to the recovery of the cuprous iodide in a sufficiently active state.

SUMMARY OF INVENTION

An object of this invention is to provide a novel process for recovering cuprous iodide from a reaction mixture obtained by reacting a halonaphthalene with a trifluoroacetate salt in the presence of cuprous iodide and a dipolar aprotic solvent.

Another object is to provide such a process wherein the cuprous iodide is recovered in a form particularly conducive to its use in further trifluoromethylation reactions.

These and other objects are attained by washing with an alcohol and a carboxylic acid and then with water the separated inorganic ingredients obtained by reacting a halonaphthalene with a trifluoroacetate salt in the presence of cuprous iodide and a dipolar aprotic solvent to form a (trifluoromethyl)naphthalene and separating out the inorganic ingredients of the final reaction mixture in the recovery of the product.

DETAILED DESCRIPTION

The inorganic residue which is subjected to the process of the invention is a residue obtained by separating out the inorganic ingredients from a (trifluoromethyl)naphthalene reaction mixture obtained by reacting a halonaphthalene corresponding to the formula:

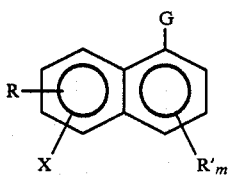

with a trifluoroacetate salt in the presence of cuprous iodide and a dipolar aprotic solvent to form a (trifluoromethyl)naphthalene corresponding to the formula:

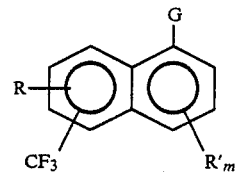

in which formulas X is bromo or iodo, R and R' are independently selected from alkyl and alkoxy groups containing 1-6 carbons, m is 0 or 1, and G is —CN or —COOR" in which R" is saturated hydrocarbyl. Such synthesis mixtures and their preparation are taught in Ramachandran et al., Lin et al., and Davidson I and II, the teachings of all of which are incorporated herein in toto by reference.

As indicated in these references, the synthesis mixtures wherein the (trifluoromethyl)naphthalene is a 6-alkoxy-5-trifluoromethyl-1-cyanonaphthalene, such as 6-methoxy-5-trifluoromethyl-1-cyanonaphthalene, or a 6-alkoxy-5-trifluoromethyl-1-naphthoate, such as methyl 6-methoxy-5-trifluoromethyl-1-naphthoate, are of particular interest because of their utility in the preparation of tolrestat-type pharmaceuticals. Moreover, in the preparation of these and similar compounds, iodo precursors have a yield advantage and bromo precursors an economic advantage, while potassium and tetraalkylammonium salts are preferred over sodium salts, and potassium salts are particularly preferred. Also, although N,N-dimethylformamide and N,N-dimethylacetamide are preferred solvents, other dipolar aprotic solvents, such as N-methylpyrrolidone, hexamethylphosphoric triamide, dimethylsulfoxide, etc., are also utilizable.

The particular manner in which the synthesis mixture is treated to separate out the inorganic ingredients during the course of recovering the product is not critical. The process of the invention is applicable to the treatment of the inorganic residue regardless of how it is obtained. However, in a preferred embodiment of the invention, the treatment is performed on an inorganic residue obtained by the alkane decantation technique taught in copending application Ser. No. 21,162 (Heidebrecht), filed Mar. 3, 1987, the teachings of which are incorporated herein in toto by reference.

In the practice of the Heidebrecht invention, the synthesis mixture, i.e., the final reaction mixture obtained upon trifluoromethylating the halonaphthalene, is first subjected to a replacement of the dipolar aprotic solvent with an alkane containing 6–12 carbons, preferably such an alkane having a boiling point in the range of T±30° C., where T is the boiling point of the dipolar solvent. The preferred alkane varies, of course, with the particular dipolar solvent in the mixture but, because of the preference for dimethylformamide and dimethylacetamide as dipolar solvents, is most apt to be octane, nonane, decane, or an alkane mixture having a similar boiling point.

The manner in which the dipolar solvent is replaced is not critical, but it is generally preferred to accomplish the replacement in a manner conducive to easy recycling of the dipolar solvent. Thus, a preferred technique is to remove a large portion, e.g., about 50-70%, of the dipolar solvent from the synthesis mixture by vacuum stripping, add the alkane, and remove the remainder of the dipolar solvent by azeotropic distillation to form a distillate from which the dipolar solvent can be recovered as a separate phase.

After replacement of the dipolar solvent has been completed, the resultant slurry of (trifluoromethyl)naphthalene, unreacted precursors, cuprous iodide, salts, and optional ingredients in an alkane medium is heated to a temperature sufficient to dissolve the organic ingredients, a temperature which is dependent on the amount of alkane medium—lower temperatures, e.g., about 25° C., being sufficient when a considerable excess of alkane is present, and higher temperatures being more suitable when the amount of alkane present is simply compatible with the amount required to disperse the solids. Reflux temperatures are ordinarily preferred.

The inorganic ingredients of the slurry are then allowed to settle, and the organic layer is decanted and cooled to precipitate the (trifluoromethyl)naphthalene. It is then sometimes desirable to repeat the decantation with heated alkane at least one more time to recover the (trifluoromethyl)naphthalene that may have settled with the inorganic ingredients.

As an alternative to the Heidebrecht process, one can obtain the inorganic residue by any of the techniques conventionally used in recovering the product of the trifluoromethylation reaction—techniques which have in common the use of suitable organic solvents to dissolve the organic ingredients and cause the inorganic ingredients to settle out. In some of these processes, as in Heidebrecht, the inorganic residue is separated out by decanting the organic layer therefrom. In other processes the inorganic ingredients are separated from the dissolved organic ingredients by filtration.

Regardless of the manner in which the inorganic ingredients have been separated out, they are washed with an alcohol and a carboxylic acid and then with water to purify the cuprous iodide. The alcohol may be aliphatic or aromatic but is most commonly an alkanol containing 1-10 carbons; the carboxylic acid also may be aliphatic or aromatic but is generally an alkanoic acid containing 1-6 carbons. Suitable alcohols include methanol, ethanol, n-propanol, isopropanol, butanol, hexanol, decanol, benzyl alcohol, etc.; examples of suitable carboxylic acids are acetic, propionic, butyric, hexanoic, trichloroacetic, benzoic, etc. The alcohol and acid washes may be simultaneous or consecutive in either order; and, when desired, either or both washes may be repeated. For example, the inorganic ingredients may be washed with an alcohol, then with an acid, then with an alcohol, and then with water; they may be washed first with an alcohol/acid mixture, then with an alcohol, and then with water; etc.

The washes may be effected at any suitable temperature, conveniently at room temperature but sometimes more satisfactorily at elevated temperatures, e.g., reflux temperatures. The particular manner in which the washes are effected can be varied to suit the convenience of the operator. For example, when the inorganic ingredients have been separated out of the final trifluoromethylation reaction mixture by filtration, it is convenient to wash them on the filter. When they have been separated out by a decantation technique, it may sometimes be more desirable to wash them by another decantation technique.

In a preferred embodiment of the invention wherein the inorganic ingredients have been separated out by a decantation technique such as the process of Heidebrecht, the cuprous iodide is purified by (1) mixing the separated inorganic ingredients with an alcohol/carboxylic acid mixture having an acid content of about 1-15 mol %, (2) allowing the insolubles to settle, (3) decanting the supernatant, (4) mixing the insolubles with an alcohol, (5) allowing settling to occur, (6) decanting the supernatant, (7) washing the sediment with water, (8) decanting the supernatant, and (9) drying the cuprous iodide residue. It is particularly preferred in this embodiment of the invention to use an isopropanol/acetic acid mixture, especially the 90/10 mixture, for the first wash and to effect the wash by refluxing the inorganic ingredients with the alcohol/acid mixture. It is also preferred to use the same alcohol in the alcohol/acid and alcohol decantations, although different alcohols can be employed if desired.

As indicated above, the residue of the alcohol decantation is washed at least once with water, and it is generally preferred to wash this residue two or three times and to decant the supernatant after each wash.

The drying of the cuprous iodide residue may be accomplished in any convenient manner, e.g., by oven drying, but is preferably effected by azeotropic drying with a suitable hydrocarbon, such as benzene, toluene, octane, nonane, etc.

The invention is advantageous as a means of recovering cuprous iodide from a trifluoromethylation reaction in a sufficiently active form for it to have utility in further trifluoromethylations.

The following examples are given to illustrate the invention and are not intended as a limitation thereof.

EXAMPLE I

Part A

A mixture of 8.5 g of 6-methoxy-5-bromo-1-cyanonaphthalene (MBCN), 30 mL of toluene, 15.6 g of cuprous iodide, and 6.5 g of potassium trifluoroacetate was heated to reflux, and about 15 mL of toluene was distilled over. An addition was made of 75 mL of N,N-dimethylformamide (DMF), and about 15 mL of liquid was distilled over until the temperature reached about 152° C. The reaction mixture was then gently refluxed at about 150°-152° C. for four hours. VPC analysis of the reaction mixture showed a 6-methoxy-5-trifluoromethyl-1-cyanonaphthalene (MTCN) content of 94.9 area %.

Part B

A 100-mL portion of nonane was added, and about 65 mL of DMF was azeotropically distilled after which the mixture was refluxed at 149°-150° C. and about 760 mm to remove further DMF. Agitation was discontinued, the cuprous iodide and other salts were allowed to settle, and the hot purple nonane layer was decanted over and set aside to cool.

Another 100 mL of nonane was added, the mixture heated to reflux and allowed to settle, and the hot purple nonane solution decanted and set aside to cool to room temperature.

After the decants stood overnight, solids crystallized and were separated from the mother liquors and dried in a vacuum oven; and the mother liquors were separately evaporated to dryness. VPC analysis showed the MTCN contents to be:
First precipitate: 97.2%
Second precipitate: 97.3%
First mother liquor: 65.8%
Second mother liquor: 86.2%

Part C

The solids left behind in the reactor after the second nonane decantation were stirred under reflux with 100 mL of isopropanol/acetic acid (90/10) for about 30 minutes, after which settling occurred. The supernatant was decanted, and subsequent decantations were sequentially performed at room temperature with 100 mL of isopropanol and 3×100 mL of water. Then 100 mL of toluene was added to the wet cuprous iodide residue, which was then dried azeotropically.

EXAMPLE II

Example I was essentially repeated except that (1) the dry cuprous iodide slurry formed in Example I, Part C, was recycled for use as the major amount of the catalyst and was supplemented with only about 1.56 g of fresh cuprous iodide and (2) only two water washes were used in the recovery of cuprous iodide from the nonane decantation residue.

VPC analysis of the reaction mixture after four hours of trifluoromethylation showed an MTCN of 95.5%.

EXAMPLE III

Example II was essentially repeated except that the dry cuprous iodide slurry recovered from Example II was recycled for use as the major amount of the catalyst and was supplemented with only about 1.56 g of fresh cuprous iodide. VPC analysis of the reaction mixture after four hours of trifluoromethylation showed an MTCN content of 95%.

EXAMPLE IV

Example III was essentially repeated except that the dry cuprous iodide slurry recovered from Example III was recycled for use as the major amount of the catalyst and was supplemented with only about 1.56 g of fresh cuprous iodide. VPC analysis of the reaction mixture after four hours of trifluoromethylation showed an MTCN content of 95.1%.

EXAMPLE V

Part A

A mixture of 65.6 g of MBCN, 95.1 g of cuprous iodide, 191.2 g of a 29.8% solution of potassium trifluoroacetate in DMF, another 303.7 g of DMF, and 30.5 g of alkane solvent (a commercial alkane mixture having a boiling range of 160°–170° C.) was heated to 154° C. and 91 cc of condensate was drained from the overhead. After four hours of reaction, 297 g of the alkane solvent was added, and 85.76 g of DMF was azeotroped off under vacuum with 18.04 g of the alkane solvent. The cuprous iodide and other salts were allowed to settle, and the organic layer was decanted at 136° C., followed by 2×293 g alkane solvent decantations at 135±5° C. The decanted solutions were combined. MTCN was crystallized upon cooling and recovered by filtration. The isolated MTCN yield was about 87.7%, based on MBCN.

Part B

The solids left in the reactor were slurried in 192 g of methanol and 25 g of acetic acid, and the slurry was stirred at ambient temperature for one hour and then allowed to settle for 30 minutes. A dark brown solution was decanted. The process was repeated with 190 g of methanol, followed by 3×300 cc of water, with the supernatant being decanted after each wash until a pH of about 5.0 was attained. Then 184.9 g of the alkane solvent was added to the resulting cuprous iodide, 103.3 g of water was azeotroped off, and 164.2 g of the alkane solvent was removed.

EXAMPLE VI

The reactor containing the cuprous iodide slurry formed in Example V, Part B, was charged with 11.4 g of fresh cuprous iodide, 65.5g of MBCN, 191.5 g of a 29.8% solution of potassium trifluoroacetate in DMF, another 305 g of DMF, and 10 g of the alkane solvent. A trifluoromethylation and workup were conducted essentially as in Example V to provide an isolated MTCN yield of 88%.

The spent cuprous iodide was treated essentially as in Example V except that an additional water wash was made, and less alkane solvent was stripped after drying the cuprous iodide by azeotroping off the water.

EXAMPLE VII

The reactor containing the cuprous iodide slurry formed in Example VI was charged with 65.5 g of MBCN, 192.8 of a 29.6% solution of potassium trifluoroacetate in DMF, and another 304.9 g of DMF. A trifluoromethylation conducted essentially as in Example VI gave a similar conversion to MTCN.

The preceding examples show that the present process for recovering the cuprous iodide residue of an alkane decantation leads to the recovery of the cuprous iodide in a sufficiently active form to make it acceptable for use in subsequent trifluoromethylation reactions. The following examples demonstrate the inferiority of other recovery techniques in this regard.

COMPARATIVE EXAMPLE A

Part A

A mixture of 8.5 g of MBCN, 30 mL of toluene, 12.6 g of cuprous iodide, and 6.45 g of potassium trifluoroacetate was heated to reflux. A 15 mL portion of solvent was distilled. The slurry was then treated with 75 mL of DMF and heated with solvent distillation until the pot temperature reached 154° C. The mixture was then heated for four hours and then allowed to cool to ambient temperature. HPLC analysis showed the conversion to be 99.6%.

Part B

A 50-mL portion of DMF was distilled off under reduced pressure, a 110-mL portion of n-octane was added, and the remaining DMF was azeotropically distilled. The resulting slurry was warmed to 120° C. and allowed to settle, after which a 90-mL portion of a light brown solution was decanted and set aside to cool.

A fresh 110-mL portion of octane was added to the residue from the first decantation, and a 100-mL dark red portion was decanted and set aside to cool.

Precipitates formed by the cooling of the two decants were separated by filtration of the slurries. The filtrates were concentrated in vacuo; and the precipitates and concentrated mother liquors were all dried at 60° C. in vacuo. The precipitates were combined and determined by HPLC analysis to have an MTCN content of 94%, and the combined mother liquors were determined to have an MTCN content of 55.5%—a combined yield of about 6.2 g (about 77.2%).

Part C

After most of the residual octane had been azeotroped off with water up to a pot temperature of 98° C., two 100-mL aqueous decants were used to purify the cuprous iodide.

Part D

The cuprous iodide/water slurry formed in Part C was treated with 1.26 g of make-up cuprous iodide, 8.5 g of MBCN, 6.45 g of potassium trifluoroacetate, and 100 mL of octane. The water was removed by azeotropic distillation, and 65 mL of octane were distilled. A 75-mL portion of DMF was added, and the mixture was distilled to 154° C. After four hours HPLC analysis indicated the conversion to be only 52%.

COMPARATIVE EXAMPLE B

Comparative Example A was essentially repeated except that the cuprous iodide/water slurry formed in Part C was treated with isopropanol prior to being used in the second trifluoromethylation reaction. Specifically, the final cuprous iodide/water slurry was treated with 100 mL of isopropanol and warmed to 70° C. with stirring, the liquid layer was decanted, and another 100-mL portion of isopropanol was used for a second decantation. When this recovered cuprous iodide was used with 1.26 g of fresh cuprous iodide to catalyze the second trifluoromethylation, HPLC analysis showed the conversion after four hours to be only 42%.

COMPARATIVE EXAMPLE C

A 3.25 g portion of potassium trifluoroacetate was added to the final reaction mixture of Comparative Example B, and the resulting mixture was refluxed for another four hours to raise the conversion to 79%. The reaction mixture was then subjected to octane and water decantations as in Comparative Example A except that, prior to water addition, two methylene chloride decantations of 100 mL each were also used, and the residual methylene chloride was azeotroped off with 150 mL of water. The water/cuprous iodide slurry was treated with 120 mL of 20% acetic acid, the supernatant was decanted, a 100-mL portion of water was added, another decantation was performed, and the residual slurry was treated with 120 mL of octane and dried azeotropically. When the dried cuprous iodide was used with 1.26 g of fresh cuprous iodide to catalyze another trifluoromethylation, HPLC analysis showed the conversion after four hours to be only 65%.

It is obvious that many variations can be made in the products and processes set forth above without departing from the spirit and scope of this invention.

What is claimed is:

1. In a process for preparing a (trifluoromethyl)naphthalene corresponding to the formula:

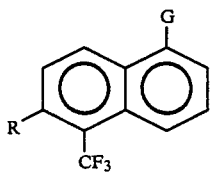

by reacting a halonaphthalene corresponding to the formula:

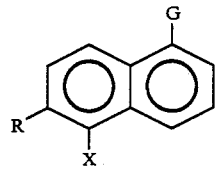

with a sodium, potassium, or trialkylammonium trifluoroacetate salt in the presence of cuprous iodide and a dipolar aprotic solvent to form the (trifluoromethyl)naphthalene and separating out the inorganic ingredients of the final reaction mixture in the recovery of the product, R in the formulas representing an alkoxy group containing 1–6 carbons, X representing bromo or iodo, and G representing —CN or —COOR" in which R" is a saturated hydrocarbyl group containing 1–10 carbons, the improvement which comprises washing the separated inorganic ingredients with an alkanol containing 1–10 carbons and an alkanoic acid containing 1–6 carbons and then with water to purify the cuprous iodide.

2. The process of claim 1 wherein the (trifluoromethyl)naphthalene is a 6-alkoxy-5-trifluoromethyl-1-cyanonaphthalene.

3. The process of claim 2 wherein the (trifluoromethyl)naphthalene is 6-methoxy-5-trifluoromethyl-1-cyanonaphthalene.

4. The process of claim 1 wherein the dipolar aprotic solvent is an amide selected from N,N-dimethylformamide and N,N-dimethylacetamide.

5. The process of claim 1 wherein the trifluoroacetate salt is potassium trifluoroacetate.

6. The process of claim 1 wherein the alcohol is isopropanol.

7. The process of claim 1 wherein the acid is acetic acid.

8. The process of claim 1 wherein the (trifluoromethyl)naphthalene product is recovered by (1) replacing the dipolar aprotic solvent in the final reaction mixture with an alkane containing 6–12 carbons, (2) heating the resultant slurry to a temperature sufficient to dissolve the organic ingredients, (3) allowing the inorganic ingredients of the slurry to settle, (4) decanting the organic layer, and (5) cooling to precipitate the (trifluoromethyl)naphthalene.

9. The process of claim 8 wherein the dipolar aprotic solvent is an amide selected from N,N-dimethylformamide and N,N-dimethylacetamide and the alkane is octane, nonane, or decane.

10. The process of claim 1 wherein the cuprous iodide is purified by (1) mixing the separated inorganic ingredients with alkanol/alkanoic acid mixture having an acid content of about 1–15 mol %, (2) allowing the insolubles to settle, (3) decanting the supernatant, (4) mixng the insolubles with an alkanol, (5) allowing settling to occur, (6) decanting the supernatant, (6) washing the sediment with water, (8) decanting the supernatant, and (9) drying the cuprous iodide residue.

11. The process of claim 10 wherein the water decantation is repeated before drying the cuprous iodide.

12. The process of claim 1 wherein the cuprous iodide is purified by washing the separated inorganic ingredients with the alkanol and alkanoic acid and then with water on a filter and subsequently drying the cuprous iodide residue.

13. In a process for preparing 6-methoxy-5-trifluoromethyl-1-cyanonaphthalene by reacting 6-methoxy-5-bromo-1-cyanonaphthalene with potassium trifluoroacetate in the presence of cuprous iodide and a dipolar aprotic solvent selected from N,N-dimethylformamide and N,N-dimethylacetamide and recovering the product by (1) replacing the amide solvent in the final reaction mixture with an alkane which is selected from octane, nonane, and decane and which has a boiling point in the range of T±30° C., where T is the boiling point of the amide solvent, (2) heating the resultant slurry to reflux temperature, (3) allowing the inorganic ingredients of the slurry to settle, (4) decanting the organic layer and cooling it to precipitate the 6-methoxy-5-trifluoromethyl-1-cyanonaphthalene, (5) adding more hot alkane to the decantation residue to dissolve any remaining organic ingredients, (6) allowing the inorganic ingredients to resettle, and (7) decanting and cooling the organic layer, the improvement which comprises:

(a) refluxing the decantation residue with an isopropanol/acetic acid mixture having an acid content of about 1–15 mol %,
(b) allowing the insolubles to settle,
(c) decanting the supernatant,
(d) mixing the insolubles with isopropanol,
(e) allowing settling to occur,
(f) decanting the supernatant,
(g) washing the sediment with water,
(h) decanting the supernatant,
(i) repeating the water decantation, and
(j) drying the cuprous iodide residue.

* * * * *